United States Patent
Wang et al.

(10) Patent No.: US 10,293,134 B2
(45) Date of Patent: May 21, 2019

(54) HUMIDIFIER FOR RESPIRATOR AND RESPIRATOR

(71) Applicant: BMC Medical Co., Ltd., Beijing (CN)

(72) Inventors: Bo Wang, Beijing (CN); Zhi Zhuang, Beijing (CN)

(73) Assignee: BMI MEDICAL CO., LTD., Beijing (CN)

( * ) Notice: Subject to any disclaimer, the term of this patent is extended or adjusted under 35 U.S.C. 154(b) by 576 days.

(21) Appl. No.: 15/083,278

(22) Filed: Mar. 28, 2016

(65) Prior Publication Data
US 2016/0206847 A1 Jul. 21, 2016

Related U.S. Application Data (63) Continuation of application No. PCT/CN2014/090941, filed on Nov. 12, 2014.

(30) Foreign Application Priority Data

Jan. 8, 2014 (CN) .......................... 2014 1 0008729

(51) Int. Cl.
*A61M 16/16* (2006.01)

(52) U.S. Cl.
CPC ....... *A61M 16/16* (2013.01); *A61M 2205/123* (2013.01); *A61M 2205/21* (2013.01)

(58) Field of Classification Search
CPC .. A61M 16/00; A61M 16/1045; A61M 16/16; A61M 16/10;
(Continued)

(56) References Cited

U.S. PATENT DOCUMENTS

| 4,993,411 A | 2/1991 | Callaway |
| 5,693,266 A * | 12/1997 | Jung ..................... B01F 3/0407 |
| | | 261/142 |

(Continued)

FOREIGN PATENT DOCUMENTS

| CN | 1153885 A | 7/1997 |
| CN | 1491124 A | 4/2004 |

(Continued)

OTHER PUBLICATIONS

Written Opinion in counterpart Chinese Application PCT/CN2014/090941, dated Feb. 13, 2015.
(Continued)

*Primary Examiner* — Scott J Medway
*Assistant Examiner* — Matthew Ryan Moon
(74) *Attorney, Agent, or Firm* — Flener IP & Business Law; Zareefa B. Flener (57) ABSTRACT

A humidifier includes a water receiving chamber enclosed by a main body and a bottom plate, the water receiving chamber is divided into a gastight liquid reservoir chamber and a heating chamber communicated with exterior environment by a vertically disposed partition plate. A passage for communicating the liquid reservoir chamber and the heating chamber is disposed adjacent to the bottom plate. A baffle extending toward the bottom plate from a top wall of the main body is disposed in the heating chamber, there is a gap between the baffle and each of a circumferential sidewall of the heating chamber and a level of liquid in the heating chamber. A circumferential sidewall of the baffle, the partition plate and the top wall collectively form a backflow tank. When the humidifier and a respirator including the humidifier are tilted, the water inside the humidifier does not flow out.

18 Claims, 6 Drawing Sheets

(58) Field of Classification Search
CPC ............ A61M 16/1075–16/109; A61M 16/14;
A61M 16/147; A61M 16/161–16/168;
A61M 2205/123; A61M 2205/21; Y10S
261/65; B01F 3/04
USPC .............................. 261/119.1, 142; 126/113
See application file for complete search history.

(56) References Cited

U.S. PATENT DOCUMENTS

| | | | |
|---|---|---|---|
| 6,749,181 | B1 | 6/2004 | Chen |
| 8,636,002 | B2* | 1/2014 | McAuley .......... A61M 16/1075 128/203.12 |
| 9,155,858 | B2* | 10/2015 | Chen ......................... B01F 3/04 |
| 9,302,068 | B2* | 4/2016 | Shelly ................... A61M 16/16 |
| 9,545,492 | B2* | 1/2017 | Dimatteo .............. A61M 16/16 |
| 2010/0071692 | A1 | 3/2010 | Porges |

FOREIGN PATENT DOCUMENTS

| | | |
|---|---|---|
| CN | 102083492 A | 6/2011 |
| CN | 102784432 A | 11/2012 |
| CN | 103800982 A | 5/2014 |
| CN | 203763627 U | 8/2014 |
| DE | 19936499 A1 | 2/2001 |
| WO | 2009/156921 A1 | 12/2009 |
| WO | 2011/086436 A1 | 7/2011 |
| WO | 2012123854 A1 | 9/2012 |
| WO | 2013/174129 A1 | 11/2013 |

OTHER PUBLICATIONS

Search Report from counterpart Chinese Application PCT/CN2014/090941, dated Feb. 13, 2015.
European Search Report from counterpart European Application 14878082.8, dated Nov. 21, 2016.
Chinese Office Action from counterpart Application 201410008729.3, dated Jun. 6, 2015.

* cited by examiner

HUMIDIFIER FOR RESPIRATOR AND RESPIRATOR

CROSS-REFERENCE TO RELATED APPLICATIONS

The present application is a continuation application of PCT International Application No. PCT/CN2014/090941 filed on Nov. 12, 2014, which claims priority to Chinese Patent Application No. 201410008729.3, filed on Jan. 8, 2014, titled "Humidifier for respirator and respirator", in the State Intellectual Property Office of China, all contents of which are incorporated by reference herein.

TECHNICAL FIELD

The present invention relates to a medical device, more particularly to a humidifier for a respirator. The present invention relates to a respirator including such a humidifier also.

BACKGROUND

For sleep apnea patients (i.e., patients with severe snoring), a very long period during which apnea lasts in sleep will cause reduced oxygen in the blood, thus the body will be in a hypoxic state. Apnea will cause sleep very shallow and fragmented, and the patient cannot get high quality sleep. Even with a ten-hour sleep, the patient doesn't get a good rest and may be exhausted in daytime, meanwhile some other serious adverse consequences may occur. If the apnea occurs frequently, over years the patient will have a series of serious physiology and pathology.

In the prior art, respirators are widely used to treat the sleep apnea. In order to provide patients with the appropriate moderate oxygen, these respirators usually include humidifiers. During use of the respirators, patients often inadvertently tilt the humidifiers, resulting in spilling of water in the humidifiers, which brings inconvenience to patients.

SUMMARY

In view of the above, the present invention provides a humidifier for a respirator. The humidifier includes a backflow tank for reserving water, so as to prevent discharging of water when the humidifier is tilted. The present invention also provides a respirator comprising such a humidifier.

According to a first aspect of the present invention, there is provided a humidifier for a respirator, comprising: a water receiving chamber enclosed by a main body and a bottom plate and divided into a gastight liquid reservoir chamber and a heating chamber communicated with exterior environment by a vertically disposed partition plate; a passage for communicating the liquid reservoir chamber and the heating chamber; and a baffle located in the heating chamber and extending toward the bottom plate from a top wall of the main body, wherein there is a gap between the baffle and a circumferential sidewall of the heating chamber, a circumferential sidewall of the baffle, the partition plate and the top wall collectively form a backflow tank.

In one embodiment, a ratio of a volume of the backflow tank to a volume of the liquid reservoir chamber is between 0.02 and 0.3.

In one embodiment, the baffle comprises a first cylindrical portion and a second cylindrical portion connected with a circumferential outer sidewall of the first cylindrical portion, the first cylindrical portion forms a gas outlet chamber, the second cylindrical portion forms a gas inlet chamber which is in communication with the gas outlet chamber.

In one embodiment, a first notch extending to a bottom end of the first cylindrical portion from a middle portion of the first cylindrical portion is formed in a part of the first cylindrical portion far away from the second cylindrical portion. A ratio of a longitudinal length of the first notch to a height of the heating chamber is between 0.1 and 0.8. A ratio of a circumferential length of the first notch to a circumferential length of the first cylindrical portion is between 0.1 and 0.8.

In one embodiment, a second notch extending to a bottom end of the second cylindrical portion from a middle portion of the second cylindrical portion is formed in a part of the second cylindrical portion far away from the first cylindrical portion. A ratio of a longitudinal length of the second notch to a height of the heating chamber is between 0.1 and 0.8. A ratio of a circumferential length of the second notch to a circumferential length of the second cylindrical portion is between 0.1 and 0.8.

In one embodiment, a gas inlet port is disposed as passing through a circumferential sidewall of the heating chamber and a circumferential sidewall of the second cylindrical portion, and the second notch is disposed below the gas inlet port. The second notch is disposed right below the gas inlet port.

In one embodiment, a heating plate is disposed on a part of the bottom plate corresponding to the heating chamber.

In one embodiment, the passage is a through-hole formed in the partition plate and adjacent to the bottom plate. Alternatively, the passage is formed by separating the partition plate from the bottom plate.

In one embodiment, a distance between the bottom plate and an end of the baffle which is adjacent to the bottom plate is greater than a distance between the bottom plate and the passage.

According to a second aspect of the present invention, there is provided a respirator comprising the above-described humidifier.

In the present application, the term "gastight liquid reservoir chamber" means that the liquid reservoir chamber is not in direct communication with exterior environment, instead it is in communication with exterior environment via the passage and the heating chamber. The term "vertically" refers to being substantially perpendicular to the bottom plate.

Compared with the prior art, the present invention has the following advantages. (1) The backflow tank is disposed in the heating chamber. When the humidifier is tilted or even turned over, the water in the heating chamber will be accumulated in the backflow tank, rather than being discharged to outside of the humidifier, which brings convenience to users. (2) The backflow tank is located inside the heating chamber and the volume thereof is controlled accurately. In this way, the volume of the humidifier is not increased due to the backflow tank, which facilitates usage of the humidifier. (3) The second notch is disposed in the second cylindrical portion, which avoids blowing away of the surface of the liquid in the heating chamber by the inlet gas with a great rate. Therefore, dry burning of the heating plate is prevented, and safety of the humidifier is improved. The first notch is disposed in the first cylindrical portion, which reduces the rate of outlet gas flow. In this way, discharging or spilling of water in the heating chamber due to the outlet gas flow is avoided. (4) The first notch and the second notch are configured to have small areas, so that the baffle can guide the gas flow from the gas inlet chamber, and the gas flow blows the water surface in the heating chamber as much as possible to take most of the water vapor away, thereby increasing the humidity of the gas.

BRIEF DESCRIPTION OF DRAWINGS

Hereinafter embodiments of the present invention will be described in more detail with reference to the accompanying drawings in which.

In the drawings, the like reference numbers designate the like components. The drawings are not made with actual scales.

DETAILED DESCRIPTION

Hereinafter embodiments of the present invention will be described further with reference to the accompanying drawings.

Figure 1:
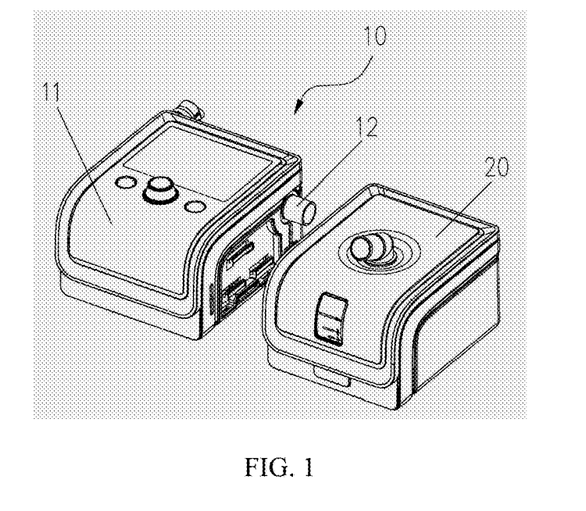
FIG. 1 is a schematic view illustrating a respirator according to an embodiment of the present invention.

FIG. 1 schematically illustrates a respirator 10 according to the present invention, which includes a host 11 and a humidifier 20. The host 11 and the humidifier 20 are connected to each other via a vent tube 12, thus gas flow generated in the host 11 can enter into the humidifier 20 through the vent tube 12. A water receiving chamber 30 which will be described in detail later is disposed inside the humidifier 20.

Figure 2:
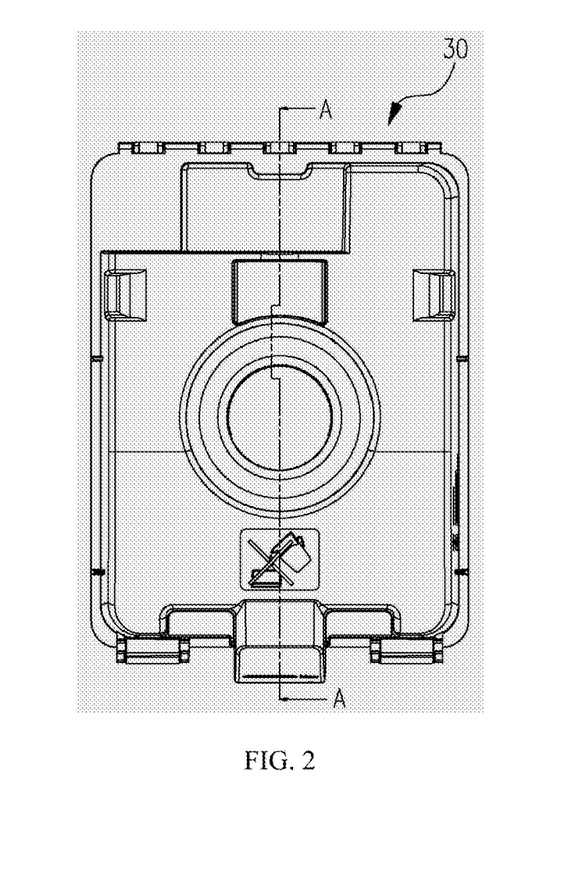
FIG. 2 is a plan view of a water receiving chamber of a humidifier according to the embodiment of the present invention.
Figure 3:
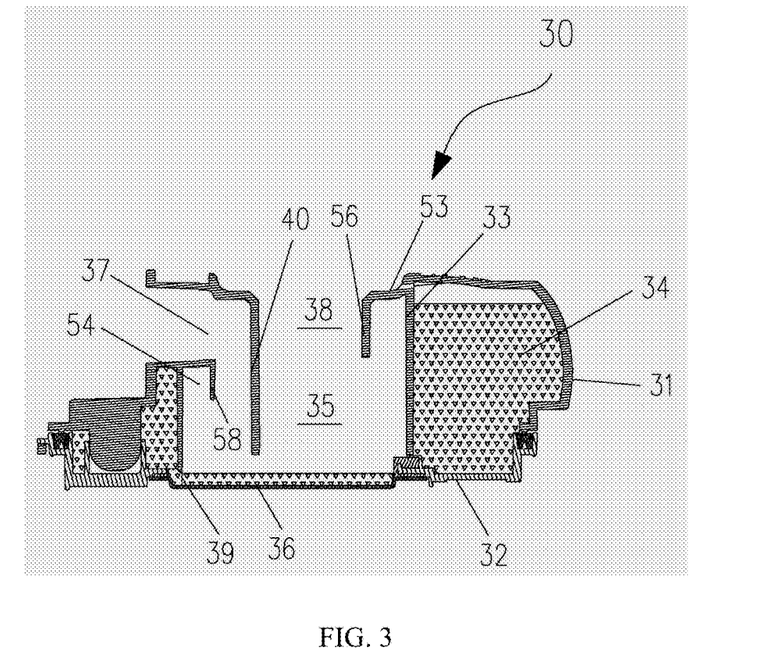
FIG. 3 is a cross-sectional view taken along line A-A of FIG. 2.
Figure 4:
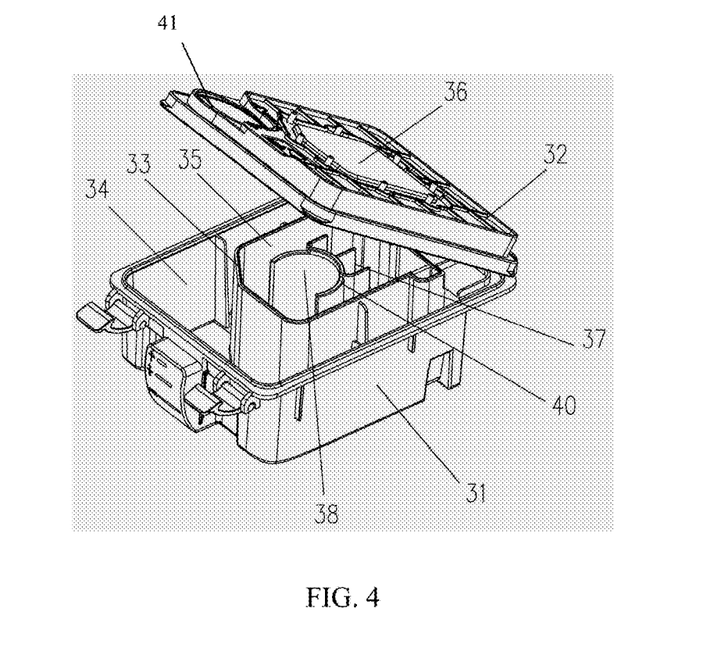
FIG. 4 is a perspective view illustrating internal structure of the water receiving chamber according to the embodiment of the present invention.

FIG. 2 is a plan view schematically illustrating the water receiving chamber 30. FIGS. 3 and 4 schematically illustrate structure of the water receiving chamber 30. Here, FIG. 3 is a cross-sectional view taken along line A-A of FIG. 2, and FIG. 4 is a perspective view of the water receiving chamber 30 according to the present invention under an inverted case to facilitate understanding. The water receiving chamber 30 is formed by enclosure of a main body 31 and a bottom plate 32. Typically the bottom plate 32 and the main body 31 are hinged so that the bottom plate 32 may be opened at any time and the inside space of the water receiving chamber 30 may be cleaned. In order to ensure seal between the bottom plate 32 and the main body 31, seal components such as silica gel pads or rubber pads may be disposed at the mating surfaces of the bottom plate 32 and the main body 31. Of course, the bottom plate 32 can be configured to be capable of being removed completely from the main body 31. For example, a plurality of snaps may be disposed at an edge of the bottom plate 32, and a plurality of snap grooves matching the plurality of snaps respectively may be disposed on the main body 31. By connection or separation of the snaps and the snap grooves, the bottom plate 32 can be connected to the main body 31 or removed therefrom. A heating plate 36 is disposed on the bottom plate 32 and used to heat water to facilitate evaporation of water.

The water receiving chamber 30 is divided into a liquid reservoir chamber 34 and a heating chamber 35 which are in fluid communication with each other by a partition plate 33 vertically disposed in the water receiving chamber 30. The partition plate 33 is a closed plate, i.e., an end of the partition plate 33 is connected to the other end thereof, so an area enclosed by the partition plate 33 forms the heating chamber 35, and an area outside the partition plate 33 forms the liquid reservoir chamber 34. The partition plate 33 may be integrally formed with the main body 31, for example through injection molding. The heating chamber 35 is configured to be in communication with the exterior environment, while the liquid reservoir chamber 34 is not in direct communication with the exterior environment, instead in fluid communication with the heating chamber 35 via a passage 39 which is located adjacent to the bottom plate 32 and passes through the partition plate 33. The passage 39 may be a through-hole formed in the partition plate 33, alternatively may be formed by separating the partition plate 33 from the bottom plate 32 (referring to FIG. 3). A water injection hole 41 is disposed in a part of the bottom plate 32 corresponding to the liquid reservoir chamber 34 (referring to FIG. 4). That is, the water injection hole 41 is disposed at the bottom end of the liquid reservoir chamber 34. A baffle 40 extending toward the heating plate 36 from a top wall 53 of the main body 31 is disposed in the heating chamber 35, and divides the heating chamber 35 into a gas inlet chamber 37 and a gas outlet chamber 38. Here, there is a gap between the baffle 40 and a circumferential sidewall of the heating chamber 35. The baffle 40 is separated from the surface of the liquid in the heating chamber 35 also, so that the gas inlet chamber 37 and the gas outlet chamber 38 are in gas communication. That is, a distance between the bottom plate 32 and an end of the baffle 40 which is adjacent to the bottom plate 32 is greater than a distance between the bottom plate 32 and the passage 39. In this way, gas flow from the host 11 can flow into the gas outlet chamber 38 through the gas inlet chamber 37 and leave the water receiving chamber 30, so as to take water vapor away during this process.

Figure 5:
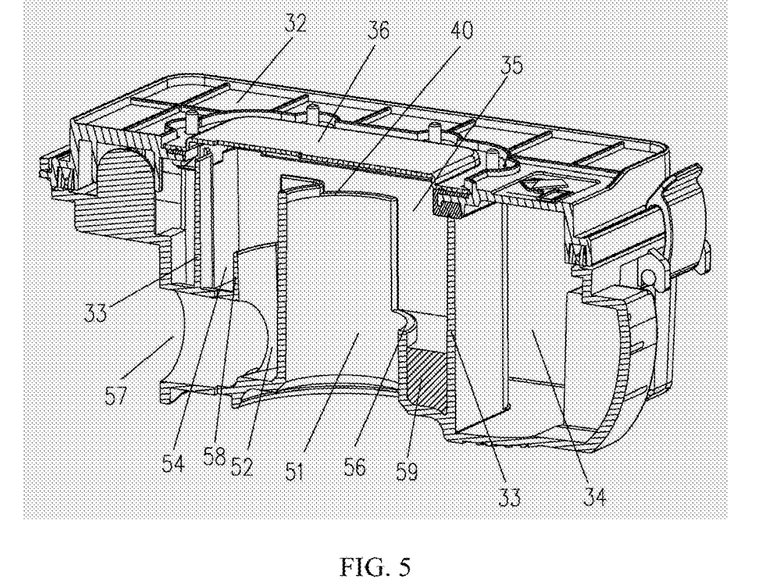
FIG. 5 is a sectional perspective view of the water receiving chamber under an inverted condition according to the embodiment of the present invention.
Figure 6:
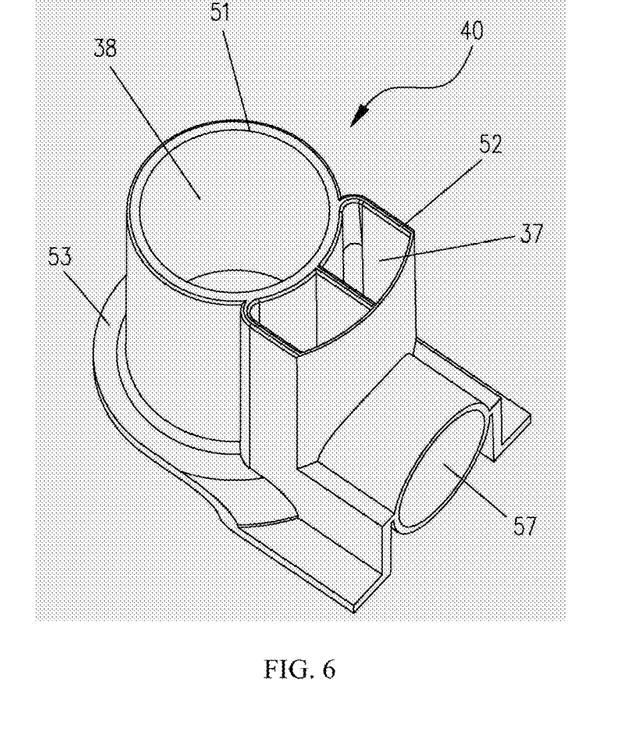
FIG. 6 is a perspective view illustrating a baffle of the humidifier according to the embodiment of the present invention.
Figure 7:
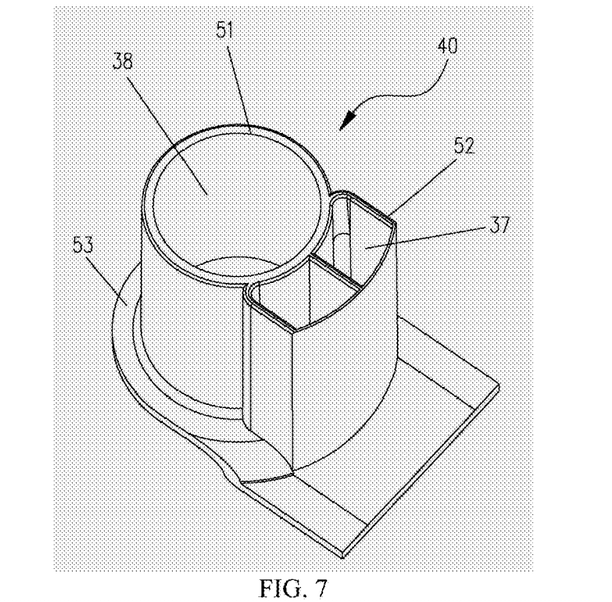
FIG. 7 is a perspective view illustrating a baffle of the humidifier according to another embodiment of the present invention.

FIG. 5 is a sectional perspective view of the water receiving chamber 30 according to the present invention when it is inverted. FIG. 6 is a perspective view of the baffle 40. In FIG. 6, in order to illustrate structure of the baffle 40 more clearly, the baffle 40 is inverted and the partition plate 33 is not shown. As shown in FIGS. 5 and 6, the baffle 40 comprises a first cylindrical portion 51 and a second cylindrical portion 52. The first cylindrical portion 51 and the second cylindrical portion 52 are connected to each other through the circumferential sidewalls thereof, so as to form an integrity, i.e. the baffle 40. The second cylindrical portion 52 forms the gas inlet chamber 37, and the first cylindrical portion 51 forms the gas outlet chamber 38. The baffle 40 is configured to be spaced apart from the circumferential sidewall of the heating chamber 35, so that the circumferential sidewall of the first cylindrical portion 51, the circumferential sidewall of the second cylindrical portion 52, the partition plate 33 (i.e., the circumferential sidewall of the heating chamber 35) and the top wall 53 collectively form a backflow tank 54. The function of the backflow tank 54 will be described in detail later. It could also be seen from FIGS. 5 and 6 that a gas inlet port 57 communicated with the vent tube 12 is disposed as passing through the circumferential sidewall of the heating chamber 35 and the circumferential sidewall of the second cylindrical portion 52, so that gas flow from the host 11 can be introduced into the humidifier 20. The sidewall of the gas inlet port 57 actually forms a part of the bottom surface of the backflow tank 54, that is, the sidewall of the gas inlet port 57 replaces the top wall 53. It can be understood that the gas inlet port 57 may be disposed in other places, such as the top wall 53 as shown in FIG. 7, instead of being disposed as passing through the circumferential sidewall of the heating chamber 35 and the circumferential sidewall of the second cylindrical portion 52.

During operation, firstly the water receiving chamber 30 is inverted (referring to FIG. 5), and then water is introduced into the liquid reservoir chamber 34 through the water injection hole 41. After injection of water, the main body 31 of the water receiving chamber 30 is placed facing upward, gas will enter into the liquid reservoir chamber 34 via the passage 39, so that water will automatically flow into the heating chamber 35 through the passage 39. When the water in the heating chamber 35 blocks the passage 39, water no longer flows into the heating chamber 35. The water in the heating chamber 35 is heated by the heating plate 36 to generate water vapor for humidifying the gas. When the passage 39 is in communicating with gas again, the gas will enter into the liquid reservoir chamber 34 through the passage 39, thus the water in the liquid reservoir chamber 34 is supplied into the heating chamber 35. It is noted that the gas mentioned in this embodiment may be pure oxygen, air or other kinds of gas which is helpful for the treatment.

Figure 8:
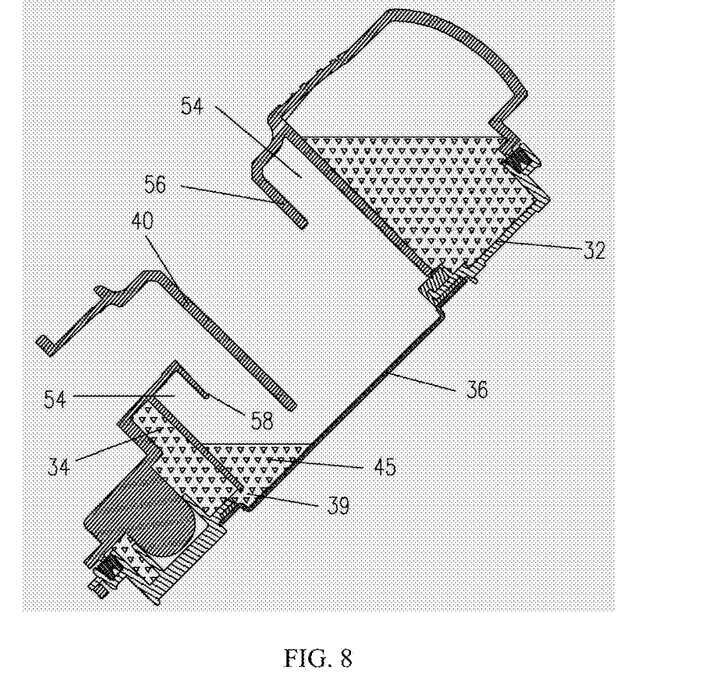
FIG. 8 is a schematic view illustrating a tilted state of the water receiving chamber of the humidifier according to an embodiment of the present invention.

If a user accidentally tilts the humidifier 20 and one end of the water receiving chamber 30 far away from the passage 39 is lifted as shown in FIG. 8, the water in the heating chamber 45 will be gathered at the passage 39, so as to block the passage 39. Under the influence of atmospheric pressure, the water no longer flows from the liquid reservoir chamber 34, which prevents spilling of water. In order to achieve a better effect, the passage 39 may be disposed as close as possible to the bottom plate 32, so that a small amount of water in the heating chamber 35 can block the passage 39. In this way, it is not required to reserve a large amount of water in the heating chamber 35.

Figure 9:
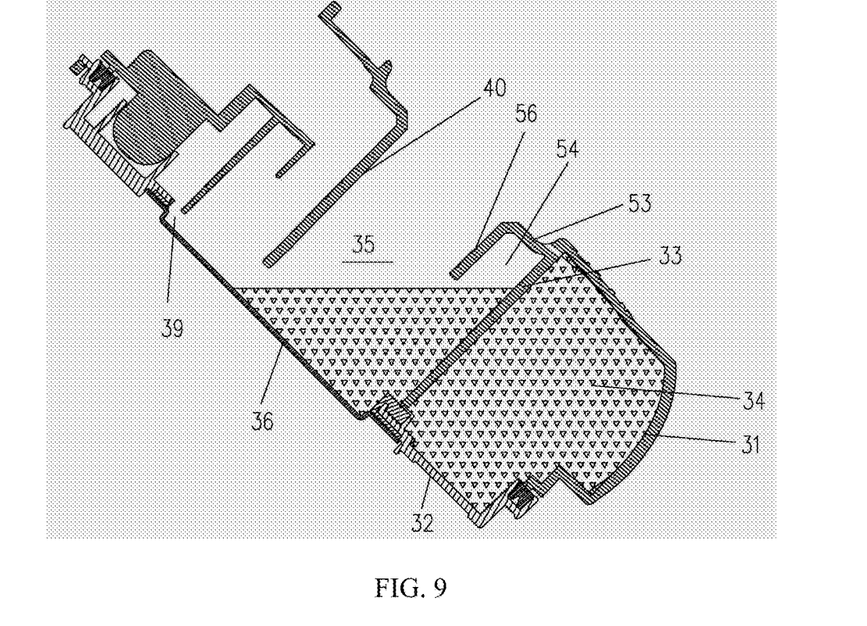
FIG. 9 is a schematic view illustrating another tilted state of the water receiving chamber of the humidifier according to an embodiment of the present invention.

FIG. 9 schematically illustrates the state of the water in water receiving chamber 30 when the humidifier 20 is tilted toward the other direction. In the present embodiment, on the contrary to the case shown in FIG. 8, one end of the water receiving chamber 30 adjacent to the passage 39 is lifted, and the water does not block the passage 39. In this case, all of the water in the heating chamber 35 will flow into the backflow tank 54, a part of the water in the liquid reservoir chamber 34 will flow into the backflow tank 54 also, until the liquid level of water in the liquid reservoir chamber 34 is even with that in the backflow tank 54. In order to prevent spilling of water, a ratio of a volume of the backflow tank 54 to a volume of the liquid reservoir chamber 34 is set as between 0.02 and 0.3. For example, when the volume of the liquid reservoir chamber 34 is 350 ml, the volume of the backflow tank 54 is 35 ml, which ensures that the backflow tank 54 can completely accommodate the water flowing from the liquid reservoir chamber 34.

Figure 10:
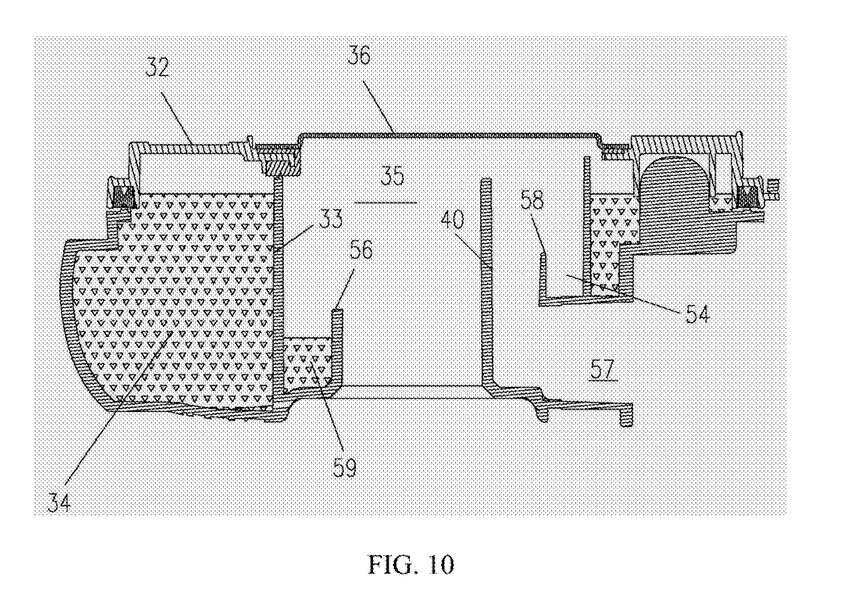
FIG. 10 is a schematic view illustrating the water receiving chamber under an inverted condition according to the embodiment of the present invention.

When the water receiving chamber 30 is completely inverted, as shown in FIG. 10, the water in the heating chamber 35 and/or a part of the water in the liquid reservoir chamber 34 will flow into the backflow tank 54. That is, water 59 will be accumulated in the backflow tank 54, which avoids spilling of water.

Figure 11:
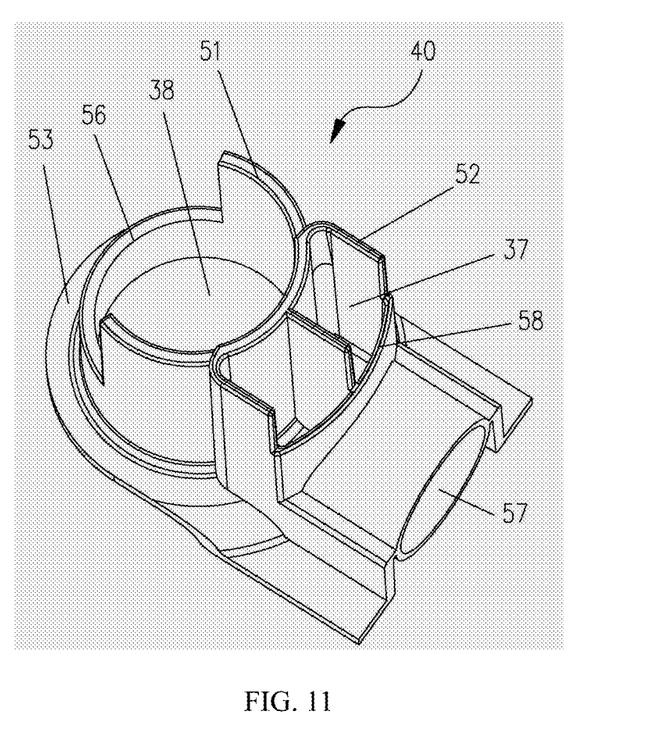
FIG. 11 is a perspective view illustrating a baffle of the humidifier according to another embodiment of the present invention.

Although the baffle 40 shown in FIGS. 8-10 has a notch (as shown in FIG. 11 and described below), it can be understood that the baffle 40 shown in FIGS. 6 and 7 can be used in the embodiment shown in FIGS. 8-10 to form the backflow tank, repeated description thereof will be omitted herein.

FIG. 11 is a perspective view illustrating a baffle different from the baffle 40 shown in FIGS. 6 and 7. It should be noted that the baffle 40 shown in FIG. 11 has the same structure as the baffle 40 shown in FIGS. 3-5 and 8-10. In the baffle 40 shown in FIG. 11, a first notch is formed in a part of the first cylindrical portion 51 far away from the second cylindrical portion 52. The first notch extends from a middle portion of the first cylindrical portion 51 to a bottom end of the first cylindrical portion 51, so that only a plate 56 with a small height is remained at the first notch of the first cylindrical portion 51. By disposing the first notch, a flow path of the outlet gas flow leaving the heating chamber 35 is widened, thereby reducing the rate of outlet gas flow. In this way, spilling of water in the heating chamber 35 due to the outlet gas flow is avoided, and thus discomfort of the patient due to water entering into the gas outlet chamber 38 is prevented.

A ratio of a longitudinal length of the first notch to a height of the heating chamber 35 is between 0.1 and 0.8. For example, the height of the heating chamber 35 is 60 mm, and the longitudinal length of the first notch is 6 mm. The first notch with such a size results in an appropriate length of the plate 56, which ensures the volume of the backflow tank 54.

A ratio of a circumferential length of the first notch to that of the first cylindrical portion 51 is between 0.1 and 0.8. For example, when the first cylindrical portion 51 is cylindrical, an opening angle of the first notch is 100°, that is, the ratio of the circumferential length of the first notch to that of the first cylindrical portion 51 is 0.28. Thus, a small area is occupied by the first notch in the first cylindrical portion 51, that is, most of the first cylindrical portion 51 is extended to proximity of the level of liquid in the heating chamber 35. Accordingly, the first cylindrical portion 51 can effectively guide the gas flow from the gas inlet chamber 37, so that the gas flow blows the water surface in the heating chamber 35 as much as possible to take most of the water vapor away, thereby increasing the humidity of the gas.

As shown in FIG. 11 also, the gas inlet port 57 is disposed as passing through the circumferential sidewall of the heating chamber 35 and the circumferential sidewall of the second cylindrical portion 52. A second notch is formed in a part of the second cylindrical portion 52 far away from the first cylindrical portion 51 and below the gas inlet port 57. The second notch extends from a middle portion of the second cylindrical portion 52 to a bottom end of the second cylindrical portion 52, so that only a plate 58 with a small height is remained at the second notch of the second cylindrical portion 52. By disposing the second notch, the gas inlet chamber 37 (i.e., inlet gas passage) is enlarged, that is, besides the volume of the second cylindrical portion 52, the gas inlet chamber 37 further includes the volume of the space between the plate 58 and the circumferential sidewall of the heating chamber 35. In this way, the inlet gas has a significantly reduced rate after entering into the gas inlet chamber 37, which avoids blowing away of the surface of the liquid in the heating chamber 35 by the inlet gas with a great rate. Therefore, dry burning of the heating plate 36 is prevented, and safety of the humidifier 20 is improved. Preferably, the second notch is disposed right below the gas inlet port 57. In this way, once the inlet gas flow enters into the gas inlet chamber 37, the rate of the inlet gas flow will be reduced immediately, which further improves safety of the humidifier 20. It can be understood that a second notch can be formed in the second cylindrical portion 52 shown in FIG. 7, detailed description thereof will be omitted herein.

A ratio of the longitudinal length of the second notch to a height of the heating chamber 35 is between 0.1 and 0.8. For example, the height of the heating chamber 35 is 60 mm, and the longitudinal length of the second notch is 36 mm. The second notch with such a size results in an appropriate length of the plate 58, which ensures the volume of the backflow tank 54.

A ratio of the circumferential length of the second notch to that of the second cylindrical portion 52 is between 0.1 and 0.8. Similar to the first notch, cooperation of the second notch with such a size and the first notch can effectively guide flow of the inlet gas flow, so that the gas flow blows the water surface in the heating chamber 35 as much as possible to take most of the water vapor away, thereby increasing the humidity of the gas.

Although the exemplary embodiments of the present invention have been described, it is understood that various changes and modifications can be made within the scope of the present invention. In particular, various features of the above-described embodiments can be mixed and matched in any manner. Therefore, the present invention is not limited to the disclosed embodiments, rather, all technical schemes within the scope of the claims are covered.

What is claimed is:

1. A humidifier for a respirator, comprising:
   a water receiving chamber enclosed by a main body and a bottom plate and divided, by a vertically disposed partition plate, into a gastight liquid reservoir chamber and a heating chamber communicated with exterior environment;
   a passage for communicating the liquid reservoir chamber and the heating chamber; and
   a baffle located in the heating chamber and extending toward the bottom plate from a top wall of the main body,
   wherein there is a gap between the baffle and a circumferential sidewall of the heating chamber, and a backflow tank is collectively formed by a circumferential sidewall of the baffle, the partition plate and the top wall,
   wherein the baffle comprises a first cylindrical portion and a second cylindrical portion connected with a circumferential outer sidewall of the first cylindrical portion, the first cylindrical portion forms a gas outlet chamber, and the second cylindrical portion forms a gas inlet chamber which is in communication with the gas outlet chamber.

2. The humidifier according to claim 1, wherein a ratio of a volume of the backflow tank to a volume of the liquid reservoir chamber is between 0.02 and 0.3.

3. The humidifier according to claim 1, wherein a first notch extending to a bottom end of the first cylindrical portion from a middle portion of the first cylindrical portion is formed in a side of the first cylindrical portion facing away from the second cylindrical portion.

4. The humidifier according to claim 3, wherein a ratio of a longitudinal length of the first notch to a height of the heating chamber is between 0.1 and 0.8.

5. The humidifier according to claim 3, wherein a ratio of a circumferential length of the first notch to a circumferential length of the first cylindrical portion is between 0.1 and 0.8.

6. The humidifier according to claim 1, wherein a second notch extending to a bottom end of the second cylindrical portion from a middle portion of the second cylindrical portion is formed in a side of the second cylindrical portion facing away from the first cylindrical portion.

7. The humidifier according to claim 6, wherein a ratio of a longitudinal length of the second notch to a height of the heating chamber is between 0.1 and 0.8.

8. The humidifier according to claim 6, wherein a ratio of a circumferential length of the second notch to a circumferential length of the second cylindrical portion is between 0.1 and 0.8.

9. The humidifier according to claim 6, wherein a gas inlet port is disposed as passing through the circumferential sidewall of the heating chamber and a circumferential sidewall of the second cylindrical portion, and the second notch is disposed below the gas inlet port.

10. The humidifier according to claim 9, wherein the second notch is disposed right below the gas inlet port.

11. The humidifier according to claim 1, wherein a heating plate is disposed on a part of the bottom plate corresponding to the heating chamber.

12. The humidifier according to claim 1, wherein the passage is a through-hole formed in the partition plate and adjacent to the bottom plate.

13. The humidifier according to claim 1, wherein the passage is formed by separating the partition plate from the bottom plate.

14. The humidifier according to claim 1, wherein a distance between the bottom plate and an end of the baffle which is adjacent to the bottom plate is greater than a distance between the bottom plate and the passage.

15. The humidifier according to claim 1, further comprising a water injection hole disposed at a bottom end of the liquid reservoir chamber.

16. A respirator, comprising a humidifier which comprises:
   a water receiving chamber enclosed by a main body and a bottom plate and divided, by a vertically disposed partition plate, into a gastight liquid reservoir chamber and a heating chamber communicated with exterior environment;
   a passage for communicating the liquid reservoir chamber and the heating chamber; and
   a baffle located in the heating chamber and extending toward the bottom plate from a top wall of the main body,
   wherein there is a gap between the baffle and a circumferential sidewall of the heating chamber, a backflow tank is collectively formed by a circumferential sidewall of the baffle, the partition plate and the top wall,
   wherein the baffle comprises a first cylindrical portion and a second cylindrical portion connected with a circumferential outer sidewall of the first cylindrical portion, the first cylindrical portion forms a gas outlet chamber, and the second cylindrical portion forms a gas inlet chamber which is in communication with the gas outlet chamber.

17. The respirator according to claim 16, wherein a first notch extending to a bottom end of the first cylindrical portion from a middle portion of the first cylindrical portion is formed in a side of the first cylindrical portion facing away from the second cylindrical portion.

18. The respirator according to claim 16, wherein a second notch extending to a bottom end of the second cylindrical portion from a middle portion of the second cylindrical portion is formed in a side of the second cylindrical portion facing away from the first cylindrical portion.

* * * * *

UNITED STATES PATENT AND TRADEMARK OFFICE
CERTIFICATE OF CORRECTION

| | |
|---|---|
| PATENT NO. | : 10,293,134 B2 |
| APPLICATION NO. | : 15/083278 |
| DATED | : May 21, 2019 |
| INVENTOR(S) | : Bo Wang et al. |

It is certified that error appears in the above-identified patent and that said Letters Patent is hereby corrected as shown below:

On the Title Page

Item (73), The Assignee:
"BMI MEDICAL CO., LTD., Beijing (CN)"

Should be changed to:
BMC Medical Co., Ltd., Beijing (CN)

Signed and Sealed this
Twenty-seventh Day of August, 2019

Andrei Iancu
*Director of the United States Patent and Trademark Office*